United States Patent [19]

Whitten et al.

[11] Patent Number: 4,681,943

[45] Date of Patent: Jul. 21, 1987

[54] 1-ACYL-1-(2-PYRIDINYL)SEMICARBA-ZIDES

[75] Inventors: Charles E. Whitten, Plymouth, Mass.; R. Garth Pews, Midland, Mich.

[73] Assignee: The Dow Chemical Company, Midland, Mich.

[21] Appl. No.: 840,359

[22] Filed: Mar. 17, 1986

Related U.S. Application Data

[63] Continuation-in-part of Ser. No. 676,892, Nov. 30, 1984, abandoned, which is a continuation-in-part of Ser. No. 465,743, Feb. 11, 1983, abandoned.

[51] Int. Cl.$^4$ ............................................. C07D 213/75
[52] U.S. Cl. ...................................... 546/306; 546/276
[58] Field of Search .......................................... 546/306

[56] References Cited

U.S. PATENT DOCUMENTS 4,048,167  9/1977  Paul et al. ............................ 544/125
4,298,602  11/1981  Pawloski .............................. 546/23
4,428,935  1/1984  Myers .................................. 514/193

FOREIGN PATENT DOCUMENTS 46-26942  8/1971  Japan ................................. 546/306

OTHER PUBLICATIONS

Potts Chem. Rev. V. 61. pp. 87–127 (1961).
Widman Chem. Berichte vol. 29, pp. 1946–1956 (1896).

Primary Examiner—Jane T. Fan
Attorney, Agent, or Firm—S. Preston Jones; Ronald G. Brookens

[57] ABSTRACT

5-Alkyl-1-(2-pyridinyl)-1H-1,2,4-triazol-3-ols are prepared in good yield by reacting an appropriate 1-acyl-1-(2-pyridinyl)-semicarbazide with a base in the presence of a non-nucleophilic solvent. The compounds so prepared are intermediates used in the preparation of insecticides. The starting semicarbazide materials are novel compounds.

2 Claims, No Drawings

1-ACYL-1-(2-PYRIDINYL)SEMICARBAZIDES

RELATIONSHIP TO PRIOR APPLICATIONS

This application is a continuation-in-part of application Ser. No. 676,892 filed Nov. 30, 1984 now abandoned which in turn is a continuation-in-part of application Ser. No. 465,743 filed Feb. 11, 1983 now abandoned.

BACKGROUND OF THE INVENTION

The present invention relates to a method of preparing 5-alkyl-1-(2-pyridinyl)-1H,2,4-triazol-3-ols and in particular to a method of preparing 5-methyl-1-(2-pyridinyl-1H-1,2,4-triazol-3-ol. The present invention also relates to novel starting materials employed in the present method.

5-Alkyl-1-(2-pyridinyl)-1H-1,2,4-triazol-3-ols are known compounds useful as chemical intermediates in the preparation of insecticides. See for example, U.S. Pat. No. 4,298,602. Prior attempts to make these valuable chemical intermediates involved reacting an appropriate 1-(2-pyridinyl)semicarbazide with an appropriate triethyl orthoester at an elevated temperature. The cost of triethyl orthoesters and the formation of significant amounts of by-products make this route of preparation commercially unacceptable.

SUMMARY OF THE INVENTION

Briefly, in accordance with the present invention, 5-alkyl-1-(2-pyridinyl)-1H-1,2,4-triazol-3-ols having the formula

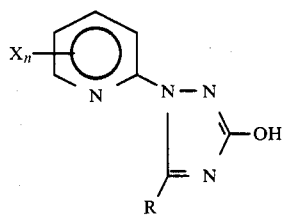

(I)

wherein
R represents $C_1$–$C_4$ alkyl;
each X independently represents Cl, F, Br, $NO_2$, $C_1$–$C_4$ alkyl, $NH_2$, mono-or dialkylamino wherein each alkyl contains from 1 to 4 carbon atoms, $C_1$–$C_4$ alkoxy, $C_1$–$C_4$ alkylthio, $C_1$–$C_4$ alkylsulfinyl, $C_1$–$C_4$ alkylsulfonyl, CN, $CF_3$, $CCl_3$, phenoxy or substituted phenoxy of the formula

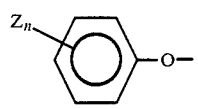

wherein
each Z independently represents Cl, F, Br, $NO_2$, CN, $C_1$–$C_4$ alkoxy, $C_1$–$C_4$ alkylthio, with the proviso that when either n is 2 or 3, all X groups are sterically compatible with each other and all Z groups are sterically compatible with each other; and
each n independently represents an integer of from 0 to 3, inclusive; are prepared in a high yield, substantially free of any by-product formation.

The present method of preparation is carried out by contacting an appropriate 1-acyl-1-(2-pyridinyl)semicarbazide corresponding to the formula

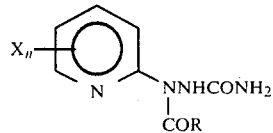

(II)

wherein X, n and R are as hereinabove defined with an inorganic base in the presence of a solvent under reaction conditions sufficient to cause formation of the desired product in a high yield. This cyclization reaction, in the hereinafter set forth solvents, is surprising in view of attempts to cyclize 1-acetyl-1-(2-pyridinyl)semicarbazide in an aqueous system which resulted in only trace amounts of the desired triazole products being formed. The products prepared by practicing the present invention are useful in making insecticides as described in U.S. Pat. No. 4,298,602.

Of particular interest in the practice of the present invention is a method of preparing 5-methyl-1-(2-pyridinyl)-1H-1,2,4-triazol-3-ol which is a valuable chemical intermediate employed in the preparation of 0,0-dimethyl 0-(1-(2-pyridinyl)-5-methyl-1H-1,2,4--triazol-3-yl)phosphorothioate and 0,0-diethyl 0-(1-(2--pyridinyl)-5-methyl-1H-1,2,4-triazol-3-yl)phosphorothioate.

DETAILED DESCRIPTION OF THE INVENTION

In the practice of the present invention it is essential to employ: an appropriate 1-acyl-1-(2--pyridinyl)semicarbazide, a base and a non-nucleophilic solvent.

When used herein the term "alkyl" is meant to encompass straight, branched and cyclic alkyl groups.

The novel 1-acyl-1-(2-pyridinyl)semicarbazide starting materials are characterized by the formula

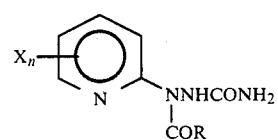

(II)

wherein
R represents $C_1$–$C_4$ alkyl;
each X independently represents Cl, F, Br, $NO_2$, $C_1$–$C_4$ alkyl, $NH_2$, mono- or dialkylamino wherein each alkyl contains from 1 to 4 carbon atoms, $C_1$–$C_4$ alkoxy, $C_1$–$C_4$ alkylthio, $C_1$–$C_4$ alkylsulfinyl, $C_1$–$C_4$ alkylsulfonyl, CN, $CF_3$, $CCL_3$, phenoxy or substituted phenoxy of the formula

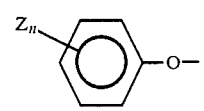

wherein
each Z independently represents Cl , F, Br, $NO_2$, CN, $C_1$–$C_4$ alkoxy, $C_1$–$C_4$ alkylthio, with the proviso that when either n is 2 or 3, all X groups are sterically compatible with each other and all Z groups are sterically compatible with each other; and each n independently represents an integer of from 0 to 3, inclusive. A preferred starting material compound is a compound of Formula I wherein n=0 and R=CH₃, i.e., 1-acetyl-1-(2-pyridinyl)-semicarbazide.

The semicarbazide starting materials are novel compounds and are prepared employing well known techniques.

The 1-acyl-1-(2-pyridinyl)semicarbazide starting materials of Formula (II) can be prepared by the reaction of an appropriate semicarbazide of the formula,

(III)

wherein X and n are as defined above, with an appropriate aliphatic acid anhydride employing standard acylation reaction conditions. Suitable aliphatic acid anhydrides include acetic anhydride, propionic anhydride, butyric anhydride and pentanoic anhydride, and, when reacted with the compounds of Formula (III) result in the formation of the corresponding 1-acetyl-1-(2-pyridinyl)semicarbazide, 1-propionyl-1-(2-pyridinyl)semicarbazide, 1-butyryl-1-(2-pyridinyl)semicarbazide and 1-pentanoyl-1(2-pyridinyl)semicarbazide, respectively.

The base employed in the practice of the present method must be soluble in the solvent and is one which is capable of abstracting a proton from the amido moiety but unreactive toward the acetyl moiety. Acceptable bases include the alkali metal hydroxides, carbonates and $C_1$–$C_4$ alkoxides such as the hydroxides, carbonates $C_1$–$C_4$ alkoxides of sodium, potassium, lithium and cesium with sodium and potassium hydroxide being the most preferred. The bases are preferably supplied at a ratio of about 1.1 moles of base per mole of semicarbazide starting material. It should be noted that the actual amount of reactants to be employed is not critical as some of the desired product is formed when employing any proportions.

The present method is conducted in the presence of a solvent which dissolves at least part of the reactants and which is unreactive toward the acetyl moiety. Acceptable solvents include secondary alcohols, tertiary alcohols and nitriles such as acetonitrile. Preferred solvents are the secondary alcohols such as, for example, isopropanol and 1-methoxy-2-propanol. The solvent is employed in an amount sufficient to dissolve the reactants which is usually from about 5 to about 50 milliliters (ml) of solvent per gram of 1-(2-pyridinyl)-semicarbazide starting material. Solvents such as water and primary alcohols have not been found to give acceptable yields of the desired product.

The present reaction is usually conducted in the liquid phase at atmospheric pressure and at temperature between about 20° C. (ambient room temperature) and the reflux temperature of the reaction mixture. It is preferred to conduct the present reaction at the reflux temperature of the reaction mixture. The reaction proceeds at lower temperatures but at a slower rate. The present reaction is typically conducted in the presence of mild agitation sufficient to cause a thorough contacting of the reactants.

In conducting the present reaction, neither the rate of addition of the reactants nor the order of addition of reactants is critical. Usually the base and solvent are mixed and heated and then the semicarbazide starting material is added to this mixture. A typical cyclization reaction generally requires from about ½ to about 24 hours, depending on the solvent. When isopropanol is employed as the solvent and the reaction is conducted at reflux, the reaction is usually complete in about one hour.

Once prepared, the desired product is recovered employing standard separatory and purification techniques. Typically, after completion of the present reaction, the reaction mixture is neutralized with a mineral acid, such as dilute HCl and cooled in an ice bath which causes a precipitate to form. The precipitate is collected and the desired product is extracted from the precipitate with an organic solvent, such as chloroform.

The present reaction can be characterized by the following chemical equation:

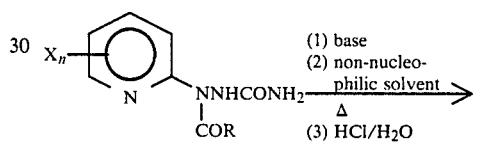

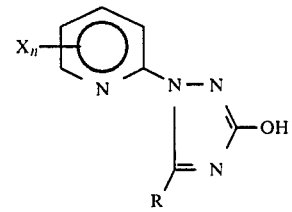

wherein X, n and R are defined hereinbefore. No attempt has been made to present a balanced equation.

In a preferred embodiment of the present invention 1-acetyl-1-(2-pyridinyl)semicarbazide is reacted with a 10% molar excess of KOH in isopropanol. The reaction is conducted at reflux temperature and the desired product 5-methyl-1-(2-pyridinyl)-1H-1,2,4--triazol-3-ol is recovered using well known procedures.

The following examples illustrate the practice of the present invention but should not be construed as limiting its scope. No attempt has been made to balance any chemical equations described herein.

EXAMPLE 1

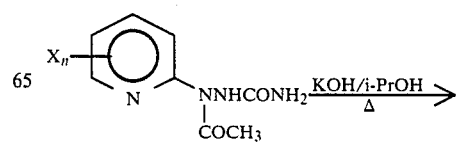

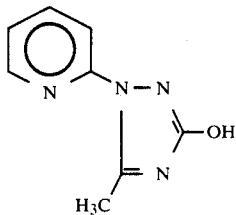

To 25 milliliters (ml) of dry isopropanol (i-PrOH) under N₂ was added 0.717 grams (g) of 86% KOH (11 mmol.) The mixture was heated to 50° C. for 20 minutes until all of the KOH had dissolved. To this mixture was added 1.94 g of 1-acetyl-1-(2-pyridyl)semicarbazide which rapidly dissolved. A precipitate formed in the reaction mixture within 10 minutes. An additional 50 ml of isopropanol was added to the reaction mixture and the mixture was heated to reflux. The precipitate that formed dissolved and the mixture became homogeneous in appearance. After 30 minutes an aliquot was removed, neutralized, and employed standard thin layer chromatography (TLC) and nuclear magnetic resonance (NMR) procedures. The presence of the desired product, i.e., 5-methyl-1-(2-pyridinyl)--1H-1,2,4-triazol-3-ol, was confirmed. The reaction mixture was neutralized with dilute aqueous HCl, and cooled to 5° C. in an ice bath. A precipitate was obtained which was filtered, washed with ether and dried in vacuo to leave 0.923 g of a white solid. The filtrates were evaporated to dryness to leave 1.3 g of white solid. The solids were combined and placed in a Soxhlet thimble and extracted with refluxing chloroform (CHCl₃) for one hour. The CHCl₃ was evaporated to leave 1.35 g of pure 5-methyl--1-(2-pyridinly)-1H-1,2,4-triazol-3-ol (confirmed by NMR). Further extraction resulted in 0.074 g of pure product. The total yield of 1.42 g represents 81% of theoretical and when corrected 5% loss in aliquoting represents 85% of theoretical.

EXAMPLE 2

1-Acyl-1-(2-pyridyl)semicarbazide

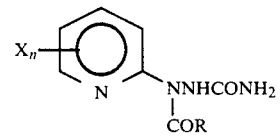

To a suspension of 3.04 g (27.9 mmol) of 1-(2-pyridyl)semicarbazide in 6 ml of acetic acid was added 2 drops of concentrated sulfuric acid followed by 2.25 g (22 mmol) of acetic anhydride. The mixture was heated to 75° C. for 20 minutes and an aliquot of the reaction mixture was withdrawn. Analysis by TLC revealed that the reaction was complete. The reaction mixture was diluted with 20 ml of water, cooled to 5° C. and filtered. The crude solid product was washed 3 times with 25 ml portions of ether and dried in vacuo to leave 1.838 g of the product as a white solid melting at 190°–193° C.

The mother liquor was evaporated to dryness, redissolved in 30 ml of a 25:5 mixture of ethanol and water, cooled to induce crystallization and allowed to stand overnight at room temperature. The precipitate was recovered and dried in vacuo. The product was recovered in a yield of 0.554 g melting at 190°–192° C. The products were combined giving a total yield of 2.39 g (61.6 percent of theoretical).

PREPARATION OF STARTING MATERIALS

The aliphatic acid anhydrides and the semicarbazides of Formula (III) used in the preparation of the novel 1-acyl-1-(2-pyridinyl)semicarbazide starting materials are well known compounds. The semicarbazides of Formula (III) are disclosed in U.S. Pat. No. 4,298,602 which is incorporated herein by reference.

We claim:
1. A compound of the formula

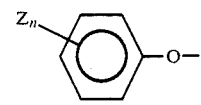

wherein
R represents $C_1$–$C_4$ alkyl;
each X independently represents Cl, F, Br, NO₂, $C_1$–$C_4$ alkyl, NH₂, mono- or dialkylamino wherein each alkyl contains from 1 to 4 carbon atoms, $C_1$–$C_4$ alkoxy, $C_1$–$C_4$ alkylthio, $C_1$–$C_4$ alkylsulfinyl, $C_1$–$C_4$ alkylsulfonyl, CN, CF₃, CCl₃, phenoxy or substituted phenoxy of the formula wherein
each Z independently represents Cl, F, Br, NO₂, CN, $C_1$–$C_4$ alkoxy, $C_1$–$C_4$ alkylthio, with the proviso that when either n is 2 or 3, all X groups are sterically compatible with each other and all Z groups are sterically compatible with each other; and
each n independently represents an integer of from 0 to 3, inclusive.
2. The compound of claim 1 wherein n is 0.

* * * * *